Aug. 6, 1940. J. H. KLUIS Plant Pat. 415
HYDRANGEA
Filed Feb. 9, 1940
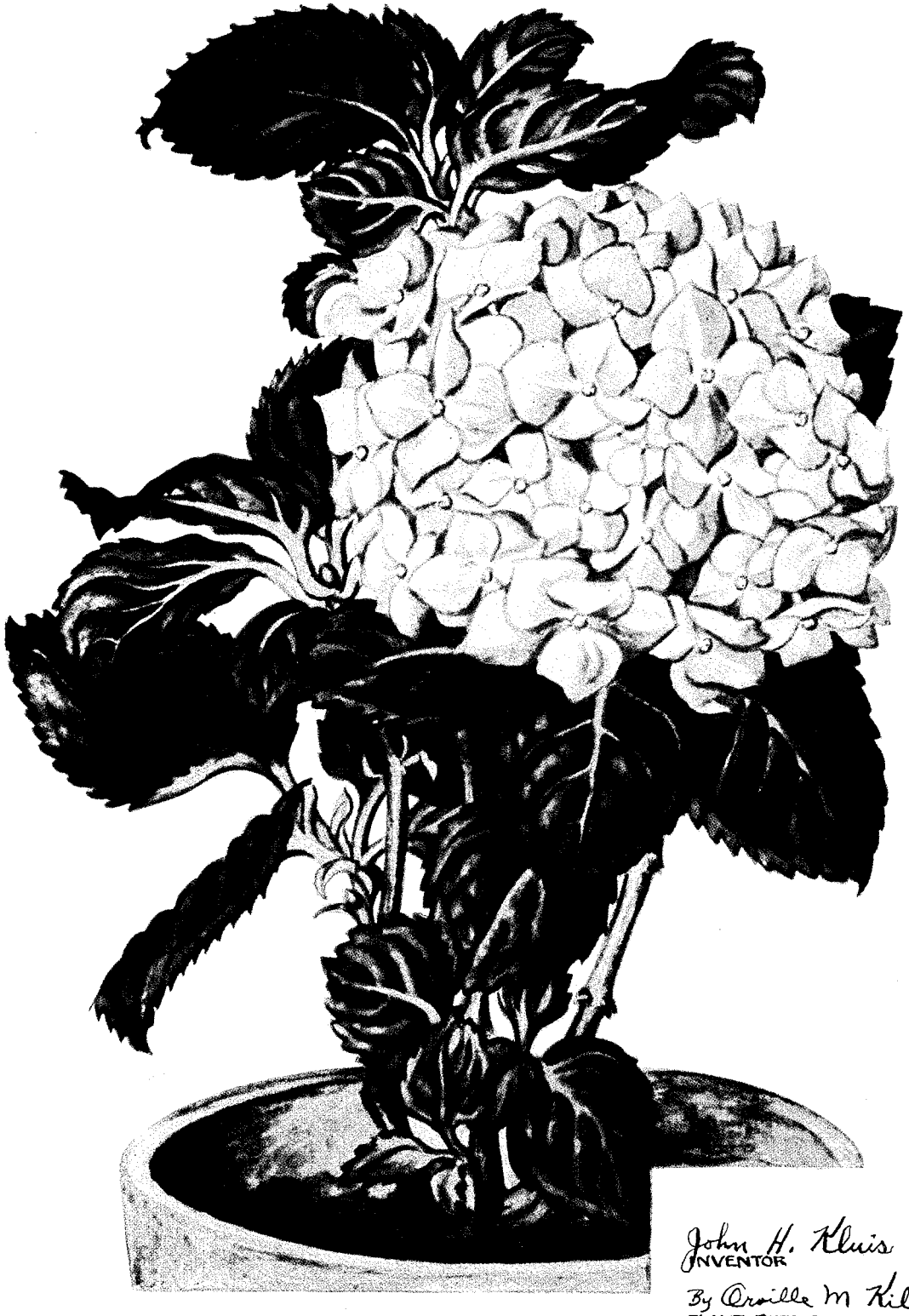
John H. Kluis
INVENTOR
By Orville M Kile
PLANT PATENT AGENT Patented Aug. 6, 1940

Plant Pat. 415

UNITED STATES PATENT OFFICE

415

HYDRANGEA

John H. Kluis, Boskoop, Netherlands, assignor to Joseph S. Merritt, Dundalk, Md.

Application February 9, 1940, Serial No. 318,140

1 Claim. (Cl. 47—60)

My present invention relates to hardy hydrangeas of the dwarf growing type and is particularly adapted to greenhouse forcing.

This new variety is the result of a cross between an unnamed seedling and Parsival, it being more like the latter variety than any other variety known to me although there are a number of differences. The most outstanding features of this new variety, which in combination differentiate it from other varieties, are its extra stiff growth, its prolific production of large trusses of striking color, its vigor and freedom of blooming, and its very dark green foliage. It is an extraordinarily free bloomer and when forced produces very large ball-shaped trusses on all the side shoots as well as on the ground shoots. It is an early and vigorous grower and when forced the stems do not need support.

Reproduction by soft wood cuttings through several generations has shown the characteristics to be permanent.

The original illustrations accompanying this application show a portion of the plant including only one truss. The plant and truss of blossoms are portrayed in approximately their true natural colors but in much reduced size.

Following is a detailed description of this new variety. Color plate references indicate Ridgway's Color Standards and Nomenclature.

*The plant*

Growth habits: Extra stiff dwarf grower. Every plant forms itself naturally without pinching or budding. Early and vigorous. Free grower. Has strong branches which do not need supports, because they are hard and stiff.

Blooming habits: When forced, all the side shoots of the branches and ground shoots produce compact, ball-shaped trusses which become very large when the plant is forced. Extraordinarily free bloomer.

Foliage: A very outstanding feature of this variety is the texture and appearance of the leaves as compared with other varieties. The texture is extremely heavy, the veins unusually prominent, and the intravenous portions puffed and ridged more than in most varieties.

*Leaves.*—Formed in close clusters of 6 or 8 leaves arranged in opposite pairs. The larger of these clusters appear at the ends of the stalks while smaller clusters of smaller leaves appear at irregular intervals along the sides of the stems. The blossoms appear to arise from the center of the terminal leaf clusters. Peduncles and stem internodes are both very short, thus forming compact leaf clusters. *Color*—unusually dark. The older foliage is between Dark Dull Yellow Green (Plate XXXII) and Dusky Yellowish Green (Plate XLI). New foliage is somewhat lighter. *Shape*—oval with acute point and base. Margin deeply and very sharply serrated. *Size*—small, fully developed leaves about 3 inches long and 2¼ inches wide. *Appearance*—glossy; very heavy; veining very prominent. Principal veins parallel each other from midrib to margin. The portion between these parallel veins is considerably raised and puffed. *Pedicels*—very short, deeply grooved.

*Stems.*—Extra stiff, hard and strong; require no supports. *Color*—Russet (Plate XV).

*The flower*

Blossom: Large, ball-shaped, compact truss, composed of many overlapping individual florets. When forced, truss attains a size up to 6 inches in diameter.

*Individual florets.*—Fertile. Composed of four or occasionally five enlarged sepals opening flat and overlapping, surrounding a center composed of a compound pistil and several stamens encased by four rudimentary cap-like petals which later open and drop off. *Sepals*—flattened when fully matured; almost round but with pointed tip. Veinings prominent; substance heavy; natural color Spinel Pink to Spinel Red (Plate XXVI), produced in various shades of blue in soils of varying acid intensity.

Having thus disclosed my invention, I claim:

The new and useful variety of dwarf hydrangea with features in combination substantially as shown and described, characterized particularly by its very dark and heavy foliage; its hardy growth; its extra stiff and strong stems and branches; its extraordinary freedom of production of large, compact, ball-shaped trusses of Spinel Pink to Spinel Red.

JOHN H. KLUIS.